(12) United States Patent
Remmereit et al.

(10) Patent No.: US 8,349,894 B2
(45) Date of Patent: Jan. 8, 2013

(54) COMPOSITIONS COMPRISING AN O/W EMULSION CONTAINING CONJUGATED LINOLEIC ACID

(75) Inventors: Jan Remmereit, Sandvika (NO); Jo Klaveness, Sandvika (NO)

(73) Assignee: Aker Biomarine ASA, Oslo (NO)

( * ) Notice: Subject to any disclaimer, the term of this patent is extended or adjusted under 35 U.S.C. 154(b) by 1050 days.

(21) Appl. No.: 10/471,049

(22) PCT Filed: Mar. 7, 2002

(86) PCT No.: PCT/GB02/00996
§ 371 (c)(1),
(2), (4) Date: Dec. 22, 2003

(87) PCT Pub. No.: WO02/070014
PCT Pub. Date: Sep. 12, 2002

(65) Prior Publication Data
US 2004/0077724 A1    Apr. 22, 2004

(30) Foreign Application Priority Data
Mar. 7, 2001 (GB) .................................. 0105622.5

(51) Int. Cl.
*A01N 37/00* (2006.01)
*A01N 43/36* (2006.01)
*A61K 31/20* (2006.01)
*A61K 31/40* (2006.01)

(52) U.S. Cl. ......................... 514/558; 514/560; 514/423

(58) Field of Classification Search .................. 514/558
See application file for complete search history.

(56) References Cited

U.S. PATENT DOCUMENTS

| | | | |
|---|---|---|---|
| 3,549,555 A * | 12/1970 | Jensen et al. | 428/402.21 |
| 3,996,355 A * | 12/1976 | Lin et al. | 514/86 |
| 4,292,310 A * | 9/1981 | Gordon et al. | 424/122 |
| 4,663,167 A * | 5/1987 | Lopez-Berestein et al. | 514/37 |
| 5,091,389 A * | 2/1992 | Ondeyka et al. | 514/291 |
| 5,710,143 A * | 1/1998 | Suzuki et al. | 514/177 |
| 5,760,083 A | 6/1998 | Cook et al. | |
| 5,837,733 A | 11/1998 | Pariza et al. | |
| 5,885,594 A | 3/1999 | Nilsen et al. | |
| 6,019,990 A | 2/2000 | Remmereit et al. | |

FOREIGN PATENT DOCUMENTS

| | | |
|---|---|---|
| EP | 0 954 975 | 11/1999 |
| EP | 1 010 424 | 6/2000 |
| FR | 2784268 | 4/2000 |
| WO | WO 96 06605 | 3/1996 |
| WO | WO 97 46118 | 12/1997 |
| WO | WO 99 08540 | 2/1999 |
| WO | WO 00 00186 | 1/2000 |
| WO | WO 00 09118 | 2/2000 |
| WO | WO 00 67596 | 11/2000 |
| WO | WO 01 08650 | 2/2001 |
| WO | WO 01 08652 | 2/2001 |

OTHER PUBLICATIONS

Remington:The Science and Practice of Pharmacy; 19th Edition; vol. I.*
Gusakova et al. (Lipophilic extracts in phytotherapy and phytocosmetics: Production and biological properties; Medicine; vol. 34, No. 4 / Jul. 1998.*
Sherman et al. (Cyclosporine in the management of corticosteroid-resistant type I autoimmune chronic active hepatitis Journal of Hepatology vol. 21, Issue 6, 1994, pp. 1040-1047).*
Strumberg et al. (Phase I Study of a Weekly 1 h Infusion of Paclitaxel in Patients with Unresectable Hepatocellular Carcinoma. European Journal of Cancer, vol. 34, No. 8, pp. 1290±1292, 1998).*

* cited by examiner

*Primary Examiner* — Sreeni Padmanabhan
*Assistant Examiner* — Layla Soroush
(74) *Attorney, Agent, or Firm* — Casimir Jones SC

(57) ABSTRACT

The present invention provides a method of treatment of a human or non-human (e.g. mammalian, avian or reptilian) animal subject by the parenteral administration of a lipophilic pharmaceutical agent, the improvement comprising administering said pharmaceutical agent in an oil-in-water emulsion containing a conjugated linoleic acid or a physiologically tolerable derivative thereof.

12 Claims, No Drawings

COMPOSITIONS COMPRISING AN O/W EMULSION CONTAINING CONJUGATED LINOLEIC ACID

This application is a 371 of PCT/GB02/00996, filed Mar. 7, 2002, the disclosure of which is incorporated herein by reference.

The present invention relates to pharmaceutical compositions comprising aqueous emulsions of conjugated linoleic acid (CLA), in particular compositions comprising a lipophilic drug disposed in the discontinuous oil phase of such emulsions.

Amphotericin B is commonly prescribed as an antifungal agent for intravenous administration to patients with systemic fungal infection, generally patients with reduced immune function such as AIDS patients and elderly patients. Amphotericin B however is not water-soluble and hence it cannot be administered as an aqueous solution, the preferred administration format for intravenously administered drugs. Liposomal formulations of amphotericin B have been proposed; however these are expensive and their production is not straightforward. Accordingly, one of the most popular ways for administering amphotericin B is by mixing with a dose of Intralipid and administering the mixture by infusion.

Intralipid is an aqueous emulsion of triglycerides, more specifically soya bean oil, which is normally used for parenteral nutrition for patients unable to take food, or sufficient food, orally. Standard dosages of Intralipid, which are given by intravenous infusion, are of the order of 500 mL of an emulsion containing 200 mg/mL of triglyceride. Such a dose involves the administration into the patient of a large quantity of saturated fat, and for the patients receiving amphotericin B this raises the risk of provoking undesirably high blood cholesterol levels.

CLA, also known as octadecadienoic acid, is a collective name for positional and geometric isomers of linoleic acid with conjugated double bonds at carbon atoms 10 and 12 or 9 and 11 in the various cis-trans configurations, i.e. cis-9, trans-11; cis-9, cis-11; trans-9, cis-11; trans-9, trans-11; cis-10, trans-12; cis-10, cis-12; trans-10, cis-12; and trans-10, trans12. CLA thus differs from ordinary linoleic acid which has double bonds at carbon atoms 9 and 12.

CLA has several unique properties, one of which is the ability to reduce the percentage of fat relative to total body mass when administered orally as a nutritional supplement. CLA is available commercially as a liquid oil from Natural ASA, Oslo, Norway under the trade name Tonalin.

We have found that aqueous suspensions/formulations of CLA can be used as a carrier for intravenously administered lipophilic drugs (such as amphotericin B) thereby avoiding the need for liposomal formulation and avoiding the undesirable exposure to high levels of saturated fatty acid triglycerides which is the consequence of formulation with Intralipid.

Thus viewed from one aspect the present invention provides a method of treatment of a human or non-human (e.g. mammalian, avian or reptilian) animal subject by the parenteral administration of a lipophilic pharmaceutical agent, the improvement comprising administering said pharmaceutical agent in an oil-in-water emulsion containing a conjugated linoleic acid or a physiologically tolerable derivative thereof.

Viewed from a further aspect the invention provides a pharmaceutical composition comprising an oil-in-water emulsion containing a lipophilic pharmaceutical agent and a conjugated linoleic acid or a physiologically tolerable derivative thereof.

Viewed from a still further aspect the invention provides the use of a conjugated linoleic acid or a physiologically tolerable derivative thereof for the manufacture of a medicament comprising an oil-in-water emulsion containing a lipophilic pharmaceutical agent and said conjugated linoleic acid or derivative thereof for use in a method of treatment involving administration of said medicament to a human or non-human (e.g. mammalian, reptilian or avian) animal subject.

Viewed from a yet further aspect the invention provides a conjugated linoleic acid or a physiologically tolerable derivative thereof for use in a method of medical treatment involving administration, particularly parenteral administration, of an oil-in-water emulsion containing said conjugated linoleic acid or derivative thereof to a human or non-human (e.g. mammalian, reptilian or avian) animal subject.

Viewed from a yet still further aspect the invention provides the use of an oil-in-water emulsion of a conjugated linoleic acid or a physiologically tolerable derivative thereof in the preparation of a medicament comprising an oil-in-water emulsion containing said conjugated linoleic acid or derivative thereof and a lipophilic pharmaceutical agent.

As used herein the term "lipophilic pharmaceutical agent" means a lipophilic compound or compound mixture which is capable of exerting a medically desired therapeutic, diagnostic or prophylactic effect, especially a therapeutic or prophylactic effect, on administration to a subject. Generally this will not be a CLA or a CLA derivative; however the term does cover CLA derivatives which are conjugates of CLA and a drug compound.

While amphotericin B is a preferred pharmaceutical agent for use according to the invention, other lipophilic agents may be used, e.g. taxol, taxoteres, griseofulvin, steroids (e.g. hydrocortisone), cyclosporin, lipid soluble vitamins (e.g. vitamin D3), HIV protease inhibitors, etc.

Indeed, while the emphasis had earlier been on water-soluble drug compounds, lipid-soluble drug compounds are nowadays becoming more attractive to pharmaceutical companies in their current drug discovery procedures.

The CLA used according to the invention may be a single compound or a mixture of two or more of the eight different CLA isomers. Generally it will be preferred to use the cis-9, trans-11 and trans-10, cis-12 isomers, on their own, in admixture or together with minor proportions (i.e. less than 50% by weight relative to total CLA) of one or more of the other isomers. Examples of CLA derivatives usable according to the invention include salts, esters (e.g. single, double or multiple esters, in particular di- and triglycerides), amides, etc.

The CLA used is preferably at least 80% wt, more preferably at least 90% wt, cis-9, trans-11 and/or trans-10, cis-12, preferably in a weight ratio of 2:98 to 98:2. For elderly patients and reduced immune function patients, the CLA is preferably at least 50% wt, more preferably at least 80% wt cis-9, trans-11. For diabetic patients or patients who are obese, who have or are at risk of cardiovascular disease or who have elevated blood cholesterol levels, the CLA is preferably at least 50% wt, more preferably at least 80% wt, trans-10, cis-12.

The preparation of CLA is described for example in U.S. Pat. No. 6,060,514 and the references cited therein, all of which are hereby incorporated by reference.

The emulsions used according to the invention are referred to as oil-in-water emulsions. By this it is meant that they contain a continuous aqueous phase and a discontinuous lipophilic phase, i.e. a CLA or CLA derivative phase. The oil droplets are preferably of micrometer size or smaller, e.g.

with mode droplet diameters in the range 50 to 100000 nm, preferably 100 to 50000 nm, especially 160 to 6000 nm, more especially 500 to 6000 nm.

The emulsions of the invention are preferably sterile and pyrogen-free. Sterile emulsions may be prepared using sterile components under sterile conditions. Alternatively the oil phase may be prepared, sterilized, then emulsified under sterile conditions with a sterile aqueous phase. As a further alternative, the emulsion may be produced and then sterilized, e.g. by heat treatment (e.g. autoclaving), by irradiation (e.g. γ-irradiation) or, where the oil droplet size is small, by sterile filtration.

The emulsions of the invention may contain further components, e.g. stabilizers, antioxidants, viscosity modifiers, vitamins, minerals, pH adjusting agents, plasma anions (e.g. $Na^+$, $Ca^{2+}$, $K^+$, especially $Na^+$ and $Ca^{2+}$, optionally deriving from their chloride salts), emulsifiers, etc.

The emulsions of the invention can be administered topically and in such cases it is preferable that the emulsion is formulated into a cream for convenient topical administration.

Examples of antioxidants that may be used include EDTA, vitamin C, vitamin E, cyclodextrins and β- and γ-derivative thereof, and α-tocopherols and derivatives thereof, e.g. salts, esters, etc. Antioxidants are preferably present in the emulsions of the invention, e.g. in amounts of 0.01 to 0.5% wt relative to total emulsion weight. The antioxidants can be added to the oil and/or water phases or to the emulsion. The use of antioxidants extends the shelf life of the emulsion product.

Where the emulsion is to be administered parenterally, it preferably has an aqueous phase which has a tonicity which is within 20% of isotonicity, more preferably within 10% of isotonicity, especially within 2% of isotonicity. Isotonicity in this regard may be taken to be 300 mOsm/kg for human subjects. This may be achieved particularly conveniently by use of physiologically tolerable salts (e.g. chloride salts) of plasma anions such as $Na^+$, $Ca^{2+}$ and $K^+$. Sodium salts and combinations of sodium and calcium salts are preferred; however non-ionic agents such as glycerol or sugars may be used to increase tonicity. Formulation in this manner has a cardioprotective effect which is especially important for aged or reduced immune function patients.

Examples of emulsifying agents that may be used in the compositions of the invention include amphiphilic compounds such as phospholipids (e.g. lecithin), polyoxyethylene sorbates (Tweens), sorbitan carboxylic acid esters (Spans), polyalkyleneoxides (e.g. PEGs and Pluronics).

Such emulsifiers are preferably used in the preparation of the emulsions of the invention and desirably are present in the emulsions in amounts of 0.02 to 10% wt relative to total emulsion weight.

pH modifying agents may be included in the compositions if this does not prejudice the stability of the pharmaceutical agent. Generally the aqueous phase of the emulsions should have a pH in the range 4.5 to 7.5, especially 5.5. to 7.0.

The emulsions of the invention preferably contain 5 to 300 mg/mL of CLA or CLA derivative, e.g. 50 to 250 mg/mL, especially 100 to 200 mg/mL and preferably have viscosities at 20° C. of 100 mPas or less. However, the emulsions may be prepared in concentrate, rather than ready-to-use, form and thus may contain for example up to 400 mg/mL CLA or CLA derivative.

The CLA or CLA derivative preferably forms the major proportion, i.e. at least 50% wt, of the oil phase in the emulsions. Particularly preferably it forms at least 70% wt, more especially at least 90% wt of the oil phase. Minor components of the oil phase may include for example the pharmaceutical agent, nutraceuticals, functional foods, antioxidants, vitamins, etc. as well as physiologically tolerable fatty acids (e.g. ω-3 acids), and mono-, di- and triglycerides. In general, each such component will generally be present as no more than 30% wt of the oil phase, e.g. 0.05 to 25% wt, preferably 0.1 to 10% wt, and the sum of such components will generally be less than 50% wt, more preferably less than about 30% wt, especially less than 10% wt of the oil phase.

The required dosage of the emulsions of the invention will vary according to the nature and concentration of the pharmaceutical agent; however dosages of between 0.5 mL and 500 mL, particularly 10 and 100 mL per 70 kg bodyweight will generally be used.

As mentioned above, the emulsions of the invention may be produced in concentrate form for dilution at the point of administration. They may also be produced as separate oil and water phases for emulsification at the point of administration. Thus the requisite components may advantageously be provided in kit form. Thus viewed from a further aspect the invention provides a kit comprising: a first container containing a sterile aqueous medium, e.g. an aqueous solution containing an emulsifier, and optionally also tonicity adjusting agents, minerals, vitamins, antioxidants, etc. as described above; a second container containing a lipophilic pharmaceutical agent and a conjugated linoleic acid or derivative thereof, optionally in an oil-in-water emulsion, and optionally containing an emulsifier and one or more other optional components as described above; and optionally instructions for the dilution or emulsification of contents of the second container with contents of the first container.

In a further embodiment, the emulsions may be prepared by admixing the pharmaceutical agent with a CLA or CLA derivative emulsion. Thus a kit comprising a CLA/CLA derivative emulsion and a separate pharmaceutical agent may be used in this regard and forms a further aspect of this invention. Viewed from this aspect the invention provides a kit comprising: a first container containing a lipophilic pharmaceutical agent, e.g. in powder (e.g. micronized) form or in solution or dispersion (e.g. in CLA or a CLA-miscible physiologically tolerable organic liquid); a second container containing an oil-in-water emulsion containing a conjugated linoleic acid or derivative thereof, and optionally further ingredients such as emulsifiers, etc. as discussed above; and optionally instructions for the dispersion of contents of the first container in contents of the second container.

The aqueous phase of the emulsions of the invention is preferably prepared using sterile pyrogen-free water, e.g. water for injections, preferably degassed before use or before admixture with the oil phase. The emulsion, or the contents of a multi-container kit, preferably have an oxygen-free gas (e.g. nitrogen or a noble gas) in the head space above the liquid or solid contents.

The emulsions of the invention may also be used to improve uptake of lipophilic drugs following oral administration or administration into body cavities having external openings or evacuation ducts, and indeed as emulsions they may improve the uptake of the CLA or CLA derivative itself. Thus the methods of treatment according to the invention extend to administration of the emulsions, optionally in packaged (e.g. encapsulated) form, into the gastrointestinal tract (e.g. oral or rectal administration or administration into the stomach via a tube), the bladder, the vagina, the uterus, the nose, or sub-lingually. Oral administration of the emulsions or of encapsulated emulsions however is preferred.

Thus viewed from a further aspect the invention provides a method of treatment of a human or non-human (e.g. mammalian, avian or reptilian) animal subject by the administration into a body cavity of said subject which is externally opening or which has an externally opening duct, of a lipophilic pharmaceutical agent, the improvement comprising administering said pharmaceutical agent in an oil-in-water emulsion containing a conjugated linoleic acid or a physiologically tolerable derivative thereof.

Viewed from a further aspect the invention also provides a pharmaceutical composition comprising an encapsulated oil-in-water emulsion containing a conjugated linoleic acid or derivative thereof and, optionally, a lipophilic pharmaceutical agent.

Encapsulation of the emulsion may for example be achieved by conventional means, e.g. using gelatin capsules, optionally internally or externally coated with a delay-release agent, e.g. a material which is insoluble at neutral pH but soluble at the pH of gastric contents, for example Eudragit of Röhm GmbH.

Administration of a CLA or CLA derivative into the gastrointestinal tract as an emulsion may increase uptake from the gut of the CLA itself as well as of any lipophilic material contained therein. Thus besides pharmaceutical agents, the emulsion may be used as a delivery vehicle for other materials which it is desired be delivered to the subject, e.g. nutraceuticals, functional foods, prebiotics, herb or other plant extracts, etc. Examples of materials which can be delivered in this way include flavones (e.g. ipriflavone), vitamins (e.g. vitamin E, vitamin D (e.g. D3), vitamin B (e.g. B12)), α-lipoic acid, biotin, minerals (e.g. chromium, zinc, iron, and selenium compounds), indoles (e.g. indole-3-carbinol), glucosamines (e.g. N-acetyl-glucosamine), essential fatty acids (e.g. EPA, DHA and ω-3 acids, e.g. DGLA), 4-hydroxyandrostenedione, amantidine, ribivarine, grape seed extract, betain, niacin, folic acid, herb extracts (e.g. rad. rubine, fructus ameos, vishagal, herb virgaurae, taraxacic, aesin, rad. rubine, and rad. taraxacic). While lipophilic agents are preferred, water-soluble agents may be included, either in the continuous aqueous phase, as micronized solids in the oil phase, or in an inner discontinuous aqueous phase, i.e. where the emulsion is a water-in-oil-in-water emulsion. Thus viewed from a further aspect the invention provides an oil-in-water emulsion pharmaceutical composition or nutritional supplement containing a conjugated linoleic acid or derivative thereof and, preferably within oil droplets of said emulsion, at least one pharmaceutical agent, nutraceutical, prebiotic, functional food or physiologically tolerable plant extract.

Typically in such emulsions the "active" additive (i.e. drug, nutraceutical, etc.) is present at 0.05 to 30% wt relative to the weight of the CLA or CLA derivative, preferably 0.1 to 10% wt.

Such emulsions will preferably be administered orally or rectally.

Typically in this aspect the emulsions can be used as nutritional supplements and/or food additives and in this way can be administered to both human and non-human animals. A preferred example of the latter is administration as a nutritional supplement to pigs.

Thus, viewed from a further aspect the invention provides a nutritional composition comprising an encapsulated oil-in-water emulsion containing a conjugated linoleic acid or derivative thereof and, optionally, a nutraceutical, prebiotic, functional food or physiologically tolerable plant extract.

Also, from a yet further aspect the invention provides a conjugated linoleic acid or a physiologically tolerable derivative thereof for use in a nutritional supplement and/or a food additive for administration to a human or non-human animal subject.

Viewed from a still further aspect the invention provides the use of an oil-in-water emulsion of a conjugated linoleic acid or a physiologically tolerable derivative therof in the preparation of a food additive or a nutritional supplement comprising an oil-in-water emulsion containing said conjugated linoleic acid or derivative therof and a nutraceutical, prebiotic, functional food or physiologically tolerable plant extract.

The emulsions may be in ready to use form or alternatively they may be in concentrate form to be diluted before administration. They may also be provided as separate "oil" and "water" compositions for emulsification prior to administration. Kits comprising concentrate or oil phase in one container and aqueous phase in another form a further aspect of the invention.

"Empty" CLA or CLA derivative emulsions, i.e. free of such "active" agents, may be loaded with the active agents after emulsion formation and those empty emulsions form a further aspect of the invention. Such empty emulsions however are preferably sterile and preferably contain an emulsifier and an antioxidant. If for use in parenteral administration, the aqueous phase is preferably produced using sterile pyrogen free water, e.g. water for injections, especially preferably water which has been degassed to reduce the oxygen content to less than 50% of that of water for injections at 1 atmosphere and 21° C., especially preferably to less than 10% and more preferably less than 2% of that oxygen content. The CLA may likewise be degassed and the emulsion is preferably made and stored in an essentially oxygen free atmosphere (e.g. less than 0.02 atmospheres oxygen partial pressure at 21° C.).

Emulsification may be achieved by conventional techniques; however the use of intensive mixers, e.g. rotor-stator or Ultra-Turrax mixers, is preferred.

The invention will now be described further with reference to the following non-limiting Examples:

EXAMPLE 1

CLA Triglyceride Emulsion for Parenteral Administration

A mixture of 10 g CLA triglyceride (produced by reacting CLA with glycerol), 1.0 g purified egg phospholipid, 50 mg sodium stearate and 5 g alpha-tocopherol is finely dispersed by using an Ultra Turrax.

A mixture of 100 ml water for injection containing 2.5 g glycerol and 0.05 mmol NaOH is added to the CLA mixture during stirring at room temperature. The mixture is homogenized in a high pressure homogenator and the final emulsion filled into vials and heat-sterilized according to generally accepted methods.

The final product is a sterile and pyrogen-free emulsion containing 10% CLA triglyceride.

EXAMPLE 2

Cyclosporin CLA Emulsion for Oral Delivery

Cyclosporin (4 g) is mixed with CLA monoglyceride (15 g) and oleyl alcohol (5 g) and heated to 80° C.

Polysorbate 80 (5 g) and water (71 g) are mixed and heated to 80° C.

The aqueous phase is added to the drug containing phase and the mixture is stirred vigorously for 5 minutes followed by homogenization using rotor-stator mixer. The CLA based emulsion contains 4% cyclosporin and is useful for oral delivery.

EXAMPLE 3

CLA Fat Emulsion

Galactolipid (1.5 g) is dispersed in CLA trigyceride mixture (20 g). The mixture is heated to 80° C.

Glycerol (2 g) and EDTA as sodium salt (0.1 g) are dissolved in water (76 g) and heated to 50° C.

The CLA phase is added to the aqueous phase under high shear mixing followed by homogenization.

The emulsion contains 20% CLA.

EXAMPLE 4

Emulsion Containing CLA Triglyceride γ-cyclodextrin Complex

A stirred mixture of γ-cyclodextrin (8 g) and CLA triglyceride (2 g) in water (20 ml) is blended for 30 minutes using an Ultra-Turrax dispenser. The mixture is stirred for 24 hours at 40° C.

The mixture is then added to Intralipid® 20% fat emulsion and the mixture is treated with an Ultra-Turrax dispenser at room temperature for 30 minutes.

EXAMPLE 5

Emulsion Containing CLA Triglyceride

CLA triglyceride (cis-9, trans-11 36.0%, trans-10, cis-12 34.7%) was prepared from refined safflower as follows. The conjugation of the acids was carried out as described in U.S. Pat. No. 5,504,114 with some modifications. The w/w/w ratios of oil/solvent/catalyst were 2/2/1. Further, propylene glycol was used instead of ethylene glycol and the temperature used for the conjugation process was 150° C. for 3 hours instead of 180° C. The CLA free fatty acids obtained were then reacted with glycerol using Novozyme 435 as a catalyst to make the triacyl glycerol. Three moles of free fatty acids were added to 1 mole of glycerol and 7% by weight of immobilised lipase. The mixture was stirred under vacuum for 48 hours at 60° C. Oil was then filtered to remove the immobilised enzymes. A mixture of this CLA trigycleride (1.50 g), L-α-phosphatidyl-choline (Egg) (Avanti Polar-Lipids Inc, USA) (120 mg) and water for injection containing 22 mg anhydrous glycerol per ml (to a total of 10 ml) was blended for 10 minutes using an Ultra-Turrax dispenser (24000 rpm) at room temperature.

A stable emulsion free from aggregates was formed during the blending.

The emulsion contained 15% w/v CLA triglyceride.

EXAMPLE 6

CLA Triglyceride Emulation Containing Amphotericin B

Amphotericin B (USP for use in parenteral products from Dumex Ltd., Denmark) (25 mg) was added to the CLA triglyceride emulsion from Example 5 (5 ml). The mixture was blended for 15 minutes using an Ultra-Turrax dispenser (24000 rpm) at room temperature.

A homogenous yellow emulsion containing 5 mg amphotericin B per ml was obtained. The emulsion was filled in a 10 ml vial with rubber stopper.

EXAMPLE 7

CLA Triglyceride Emulsion Containing Vitamin E

Vitamin E (97%, Aldrich) (36 mg) was added to the CLA triglyceride emulsion from Example 5 (5 ml). The mixture was blended for 5 minutes using an Ultra-Turrax dispenser (24000 rpm) at room temperature.

The emulsion was filled in a 10 ml vial with rubber stopper.

EXAMPLE 8

Emulsion Containing CLA-triglyceride and CLA-ethyl Ester

Cis-9, trans-10 free. fatty acid concentrate and the trans-10, cis-12 fatty acid ethyl ester concentrate were prepared as described in Berdeaux et al., JAOCS, 75 no.12 (1998), the only difference being that ethanol was used instead of methanol in preparing the alkylester of the trans-10, cis-12 concentrate. A mixture of CLA triglyceride (same as in Example 5) (740 mg), CLA ethyl ester (cis-9, trans-11 0.2%, trans-10, cis-12) (1.04 g), L-α-phosphatidylcholine (Egg) (Avanti Polar Lipids Inc., USA) (160 mg) and water for injection containing 22 mg anhydrous glycerol per ml (to a total volume of 20 ml) was blended for 10 minutes using an Ultra-Turrax dispenser (24000 rpm) at room temperature.

A stable emulsion free from aggregates was formed during the blending.

The emulsion contained 37 mg CLA triglyceride and 53 mg CLA ethyl ester per ml.

EXAMPLE 9

CLA Emulsion Containing Iron (3+) Sorbitol Citric Acid Complex and Vitamin E

Jectofer® (50 mg iron sorbitol citric acid complex per ml from Astra Zeneca) (2 ml) was added to CLA triglyceride/ethyl ester emulsion from Example 8 (5 ml). Vitamin E (97%, Aldrich) (30 ml) was added and the mixture was blended from 5 minutes using an Ultra-Turrax dispenser (24000 rpm) at room temperature.

A stable emulsion free from aggregates was formed during the blending.

The brown emulsion contained 30 mg iron sorbitol citric acid complex per ml.

EXAMPLE 10

Emulsion Containing Soya Oil. CLA Triglyceride and CLA Ethyl Ester

A mixture of CLA triglyceride (same as in Example 5) (1.0 g), CLA ethyl ester (same as in Example 8) (1.0 g), Vitamin E (97%, Aldrich) 81 mg and Intralipid (100 mg/ml from Fresenius Kabi AB, Uppsala, Sweden) to a total volume of 20 ml was blended using an Ultra-Turrax dispenser (24000 rpm) for 10 minutes at room temperature.

The emulsion contained 0.1 g CLA triglyceride/ethyl ester per ml.

EXAMPLE 11

Emulsion Containing CLA Triglyceride and Cod Liver Oil for Oral Administration

A mixture of CLA triglyceride (same as in Example 5) (3.85 g), cod liver oil (Möller's Omega-3 tran, from Peter Möller, Oslo, Norway) (6.11 g), L-α-phosphatidylcholine (P-5394, Sigma) (1.3 g) and 25 g water was blended for 30 minutes using an Ultra-Turrax dispenser (24000 rpm). Orange flavour (NO 300004 H from Givaudan Roure BV, The Netherlands) (20 drops) was added and the mixture was blended for another minute.

The product was a cream-white emulsion with no taste of cod liver oil.

The emulsion contained approximately 10% CLA triglyceride.

EXAMPLE 12

Vitamin Concentrate in Emulsion of Soya Oil and CLA Triglyceride

A complete mixture of fat-soluble and water-soluble vitamins was prepared by dissolving a mixture of water-soluble vitamins (Soluvit® powder for infusion solution prepared by Fresenius Kabi AB) one vial in lipid emulsion containing fat soluble vitamins (Vitalipid® Adult for Fresenius Kabi AB) (one vial 10 ml). CLA triglyceride (same as in Example 5) (1.0 g) and L-α-phosphatidylcholine (P-5394, Sigma) (100 mg) were added and the mixture was blended for 20 minutes using an Ultra-Turrax dispenser at room temperature.

The mixture of vitamins in the fat emulsion can be diluted with fat emulsions before use.

Typical fat emulsions for dilution of this vitamin concentrate could be CLA fat emulsions like Example 5 or fat emulsions containing other fat products.

EXAMPLE 13

Oral Emulsion Containing Vitamin C

L(+)Ascorbic acid (99%, Aldrich) (1.0 g) was added to a CLA-triglyceride/cod liver oil emulsion (from Example 11) (10 g). The mixture was blended for 2 minutes using Ultra-Turrax dispenser. The emulsion contained 100 mg Vitamin C per ml. The emulsion tasted of Vitamin C.

EXAMPLE 14

Oral Emulsion Containing L(−)Ascorbic Acid 6-palmitate

The product was made in a similar fashion to Example 13 using L(−)Ascorbic acid 6-palmitate (95%, Aldrich) (1.0 g). The emulsion did not taste of Vitamin C.

EXAMPLE 15

Dermal Cream Containing CLA Triglyceride

Unguentum M (Hermal, Kurt Herrmann, Reinbek, Germany) (12 g) and CLA triglyceride (5.6 g) were mixed using mortar and pestle. The cream thus formed can be used as the basis for dermal pharmaceutical products and as the basis for cosmetic products. Such products can be made by mixing pharmaceuticals or other compounds into the cream.

The invention claimed is:

1. A method of treatment of a human or non-human animal subject with a fungal infection by the parenteral administration of a lipophilic pharmaceutical agent comprising administering a composition comprising a lipophilic pharmaceutical agent in an oil-in-water emulsion containing a conjugated linoleic acid (CLA), wherein said conjugated linoleic acid forms at least 50% by weight of the oil in the emulsion, wherein said lipophilic pharmaceutical agent is griseofulvin.

2. The method as claimed in claim 1, wherein said CLA is a single compound.

3. The method as claimed in claim 1, wherein said CLA is a mixture of two or more CLA isomers.

4. The method as claimed in claim 1, wherein said CLA is the cis-9, trans-11 isomer and/or the trans-10, cis-12 isomer.

5. The method as claimed in claim 4, wherein said isomers are at least 80% wt cis-9, trans-11 and/or trans-10, cis-12.

6. The method as claimed in claim 5, wherein said cis-9, trans-11 and trans-10, cis-12 isomers are in a weight ratio of from 2:98 to 98:2.

7. The method as claimed in claim 1, wherein said CLA forms at least 90% wt of the oil phase in said emulsion.

8. The method as claimed in claim 1, wherein said CLA is provided as a salt, ester or amide thereof.

9. The method as claimed in claim 1, wherein oil droplets in said oil-in-water emulsions have mode droplet diameters in the range 160 to 6000 nm.

10. The method as claimed in claim 1, wherein said emulsion contains 5 to 300 mg/mL of CLA or CLA derivative.

11. The method as claimed in claim 10, wherein said emulsion contains 100 to 200 mg/mL of CLA or CLA derivative.

12. The method as claimed in claim 1, wherein said emulsion has a viscosity at 20° C. of 100 mPas or less.

* * * * *